United States Patent

Almen et al.

[11] Patent Number: 5,882,628
[45] Date of Patent: Mar. 16, 1999

[54] CONTRAST MEDIA

[75] Inventors: Torsten Almen, Falsterbo; Sven Andersson, Lomma; Lars-Goran Wistrand, Lund, all of Sweden; Klaes Golman, Rungsted Kyst, Denmark; Oyvind Antonsen, Gjesaen, Norway; Rune Fossheim, Oslo, Norway; Unni Nordby Wiggen, Rasta, Norway; Hakan Wikstrom, Groningen, Netherlands; Tomas Klingstedt, Lund, Sweden; Ib Luenbach, Dragor, Denmark; Arne Berg, Blommenholm; Harald Dugstad, Oslo, both of Norway

[73] Assignee: Nycomed Imaging AS, Oslo, Norway

[21] Appl. No.: 470,042

[22] Filed: Jun. 6, 1995

[30] Foreign Application Priority Data

Sep. 23, 1994 [GB] United Kingdom ................ 9419203.6

[51] Int. Cl.$^6$ .......................... A61K 49/00; C07C 233/03
[52] U.S. Cl. ...................... 424/9.452; 564/153; 514/546; 514/751; 514/754; 560/130; 560/141; 560/142
[58] Field of Search .................. 424/9.452; 564/153; 560/130, 141, 142; 514/546, 751, 754

[56] References Cited

U.S. PATENT DOCUMENTS

| 4,021,481 | 5/1977 | Almen et al. | 424/5 |
|---|---|---|---|
| 4,314,055 | 2/1982 | Hoey et al. | 536/53 |
| 4,348,377 | 9/1982 | Felder et al. | 424/5 |
| 4,364,921 | 12/1982 | Speck et al. | 424/5 |
| 5,047,228 | 9/1991 | Gries et al. | 424/5 |
| 5,308,607 | 5/1994 | Josef et al. | 424/5 |
| 5,616,798 | 4/1997 | Zrihen et al. | 564/153 |
| 5,618,977 | 4/1997 | Dugast-Zrihen et al. | 564/153 |
| 5,663,413 | 9/1997 | Uggeri et al. | 560/59 |

FOREIGN PATENT DOCUMENTS

| 92/141135 | 6/1992 | Australia. |
|---|---|---|
| 603 923 | 6/1994 | European Pat. Off.. |
| 1 375 139 | 11/1974 | United Kingdom. |
| 88/09328 | 12/1988 | WIPO. |
| 90/11094 | 10/1990 | WIPO. |
| 91/13636 | 9/1991 | WIPO. |
| 93/10078 | 5/1993 | WIPO. |
| 94/14478 | 7/1994 | WIPO. |
| WO 95/15307 | 6/1995 | WIPO. |

OTHER PUBLICATIONS

Hebky et al., *Coll. Czech. Chem. Comm.*, 41:3094–3105 (1976).
Hebky et al., *Coll. Czech. Chem. Comm.*, 35:667–674 (1970).
Almén, *Invest. Radiol.*, 20(Suppl. 1):S2–S9 (1985).

Primary Examiner—Shailendra Kumar
Attorney, Agent, or Firm—Bacon & Thomas PLLC

[57] ABSTRACT

The invention provides low viscosity iodinated aryl compounds, useful as X-ray contrast agents, of formula I

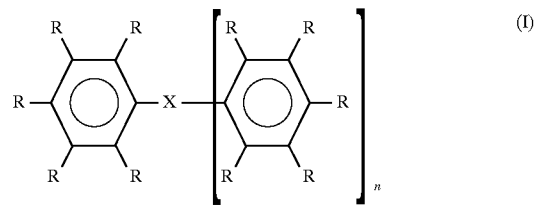

(wherein n is 0 or 1, and where n is 1 each $C_6R_5$ moeity may be the same or different; each group R is a hydrogen atom, an iodine atom or a hydrophilic moiety M or $M_1$, two or three non-adjacent R groups in each $C_6R_5$ moiety being iodine and at least one, and preferably two or three, R groups in each $C_6R_5$ moiety being M or $M_1$ moieties; X denotes a bond or a group providing a 1 to 7 atom chain linking two $C_6R_5$ moieties or, where n is 0, X denotes a group R; each M independently is a non-ionic hydrophilic moiety; and each $M_1$ independently represents a $C_{1-4}$alkyl group substituted by at least one hydroxyl group and optionally linked to the phenyl ring via a carbonyl, sulphone or sulphoxide group, at least one R group being an $M_1$ moiety; with the proviso that where n is zero either at least one $M_1$ group other than a hydroxymethyl or 1,2-dihydroxyethyl group is present or then if one hydroxymethyl or 1,2-dihydroxyethyl $M_1$ group is present at least one nitrogen-attached or hydroxylated-$C_{3-4}$ alkyl moiety-containing M group is also present) and isomers thereof.

13 Claims, No Drawings

CONTRAST MEDIA

FIELD OF THE INVENTION

This invention relates to improvements in and relating to contrast media, and in particular iodinated X-ray contrast media.

BACKGROUND OF THE INVENTION

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging, the contrast media function by modifying the X-ray absorption characteristics of the body sites into which they distribute.

Clearly however the utility of a material as a contrast medium is governed largely by its toxicity, by its diagnostic efficacy, by other adverse effects it may have on the subject to which it is administered, and by its ease of storage and ease of administration.

Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse biological effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:
  the chemotoxicity of the contrast agent,
  the osmolality of the contrast medium, and
  the ionic composition (or lack thereof) of the contrast medium.

In coronary angiography, for example, injection into the circulatory system of contrast media has been associated with several serious effects on cardiac function. These effects are sufficiently severe as to place limitations on the use in angiography of certain contrast media.

In this procedure, for a short period of time a bolus of contrast medium rather than blood flows through the circulatory system and differences in the chemical and physicochemical nature of the contrast medium and the blood that it temporarily replaces can give rise to undesirable effects, e.g. arrhythmias, QT-prolongation, and, especially, reduction in cardiac contractile force and occurrence of ventricular fibrillation. There have been many investigations into these negative effects on cardiac function of infusion of contrast media into the circulatory system, e.g. during angiography, and means for reducing or eliminating these effects have been widely sought.

Early injectable ionic X-ray contrast agents, based on triiodophenylcarboxylate salts, were particularly associated with osmotoxic effects deriving from the hypertonicity of the contrast media injected.

This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic make-up separately or together reduce the contractile force of the muscle cells and cause dilation of small blood vessels and a resultant decrease in blood pressure.

The osmotoxicity problem was addressed by the development of the non-ionic triiodophenyl monomers, such as iohexol, which allowed the same contrast effective iodine concentrations to be attained with greatly reduced attendant osmotoxicity effects.

The drive towards reduced osmotoxicity led in due course to the development of the non-ionic bis(triiodophenyl) dimers, such as iodixanol, which reduce osmotoxicity associated problems still further allowing contrast effective iodine concentrations to be achieved with hypotonic solutions.

This ability to achieve contrast effective iodine concentrations without taking solution osmolality up to isotonic levels (about 300 mOsm/kg $H_2O$) further enabled the contribution to toxicity of ionic imbalance to be addressed by the inclusion of various plasma cations, as discussed for example in WO-90/01194 and WO-91/13636 of Nycomed Imaging AS.

However X-ray contrast media, at commercial high iodine concentrations of about 300 mgI/ml, have relatively high viscosities, ranging from about 15 to about 60 mPas at ambient temperature with the dimeric media generally being more viscous than the monomeric media. Such viscosities pose problems to the administrator of the contrast medium, requiring relatively large bore needles or high applied pressure, and are particularly pronounced in paediatric radiography and in radiographic techniques which require rapid, bolus administration, e.g. in angiography.

SUMMARY OF THE INVENTION

The present invention addresses the viscosity problem encountered with the prior art materials and thus viewed from one aspect the invention provides iodinated aryl compounds, useful as X-ray contrast agents, of formula I

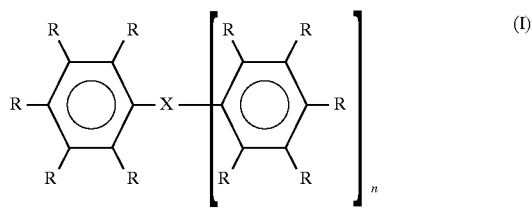

(wherein n is 0 or 1, and where n is 1 each $C_6R_5$ moiety may be the same or different; each group R is a hydrogen atom, an iodine atom or a hydrophilic moiety M or $M_1$, two or three non-adjacent R groups in each $C_6R_5$ moiety being iodine and at least one, and preferably two or three, R groups in each $C_6R_5$ moiety being M or $M_1$ moieties; X denotes a bond or a group providing a 1 to 7, for example 1, 2, 3 or 4 atom chain linking two $C_6R_5$ moieties or, where n is 0, X denotes a group R; each M independently is a non-ionic hydrophilic moiety; and each $M_1$ independently represents a $C_{1-4}$alkyl group substituted by at least one hydroxyl group and optionally linked to the phenyl ring via a carbonyl, sulphone or sulphoxide group, at least one R group, preferably at least two R groups and especially preferably at least one R group in each $C_6R_5$ moeity, being an $M_1$ moiety; with the proviso that where n is zero either at least one $M_1$ group other than a hydroxymethyl or 1,2-dihydroxyethyl (and optionally other than any hydroxyethyl) group is present or then if one hydroxymethyl or 1,2-dihydroxyethyl $M_1$ group (and optionally any hydroxyethyl group) is present at least one nitrogen-attached hydroxylated alkyl (preferably $C_{1-4}$- alkyl) moiety-containing M group is also present) and isomers, especially stereoisomers and rotamers, thereof.

DETAILED DESCRIPTION OF THE INVENTION

It is found that the compounds of the invention exhibit advantageously low viscosity in aqueous solution; this is thought to derive from the presence of $M_1$ groups on the phenyl groups, from compound asymmetry and, in the dimer compounds, from the nature of the linker X (especially where X provides a linkage less than 5 atoms in length).

Thus for example all of the water-soluble monomer compounds according to the invention that have been tested have exhibited viscosities lower than that of iohexol.

The compounds of formula I are preferably asymmetric. For the monomer compounds (where n=0) this may be achieved by asymmetric substitution of the phenyl ring. For the dimers this can be achieved by the use of an asymmetric 2 or more atom chain-forming group X and/or by selection of non-identical $C_6R_5$ groups, i.e. by non-identical substitution of the iodophenyl end groups. Asymmetric molecules are preferred as they have been found to have better water-solubility.

Such non-identical substitution of the phenyl end groups, the $C_6R_5$ moieties, may be achieved by having different numbers or positions of iodine substitution and/or by different numbers, positions or identities of M or $M_1$ substitution. To maximize iodine loading, triodophenyl end groups, i.e. groups of formula

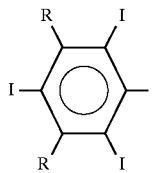

are preferred, and in these the two R groups may be the same or different, although preferably both represent M or $M_1$ groups.

Where a phenyl end group is disubstituted by iodine, it is preferably of formula

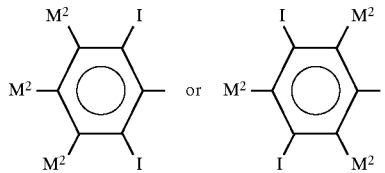

(where each $M^2$ may be the same or different and represents an $M_1$ or M group, at least one on each ring preferably representing an $M_1$ group).

Generally, diiodophenyl-diiodophenyl dimers will be less preferred than the diiodophenyl-triiodophenyl or triiodophenyl-triiodophenyl dimers, due primarily to their reduced iodine loading, i.e. 4 rather than 5 or 6 iodines per dimer molecule. Indeed the triiodophenyl-triiodophenyl dimers are generally preferred due to their higher iodine loading.

For the monomers, the triiodophenyl compounds are again preferred.

The solubilizing groups M may be any of the non-ionizing groups conventionally used to enhance water solubility. Suitable groups include for example straight chain or branched $C_{1-10}$-alkyl groups, preferably $C_{1-5}$ groups, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide linkage such as hydroxyalkylaminocarbonyl, N-alkylhydroxyalkylaminocarbonyl and bishydroxyalkylaminocarbonyl groups. Preferred among such groups are those containing 1, 2, 3, 4, 5 or 6, especially 1, 2 or 3, hydroxy groups, e.g.

—$CONH$—$CH_2CH_2OH$
—$CONH$—$CH_2CHOHCH_2OH$
—$CONH$—$CH(CH_2OH)_2$
—$CON(CH_2CH_2OH)_2$ as well as other groups such as —$CONH_2$
—$CONHCH_3$
—$OCOCH_3$
—$N(COCH_3)H$
—$N(COCH_3)C_{1-3}$-alkyl
—$N(COCH_3)$-mono, bis or tris-hydroxy $C_{1-4}$-alkyl
—$N(COCH_2OH)$-mono, bis or tris-hydroxy $C_{1-4}$-alkyl
—$N(COCH_2OH)_2$
—$CON(CH_2CHOHCH_2OH)(CH_2CH_2OH)$
—$CONH$—$C(CH_2OH)_3$ and
—$CONH$—$CH(CH_2OH)(CHOHCH_2OH)$.

In general, the M groups will preferably each comprise a polyhydroxy $C_{1-4}$-alkyl group, such as 1,3-dihydroxyprop-2-yl or 2,3-dihydroxyprop-1-yl.

Other such M groups as are conventional within the field of triiodophenyl X-ray contrast agents may also be used and the introduction of M groups onto iodophenyl structures may be achieved by conventional techniques.

In general, $M_1$ groups preferably comprise $C_{1-4}$-alkyl groups substituted by 1, 2, 3 or 4 hydroxy groups (e.g. hydroxymethyl, 2-hydroxyethyl, 2,3-bishydroxypropyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$).

In the dimeric compounds of the invention, the linker group X is conveniently a bond or a 1 to 7, eg 1, 2, 3 or 4, membered chain comprising carbon, nitrogen, oxygen or sulphur atoms, e.g.

a bond,
a O, S, N or C one atom chain,
a NN, NC, NS, CC or CO two atom chain,
or a NCN, OCN, CNC, OCO, NSN, CSN, COC, OCC or CCC three atom chain,
for example:
an oxygen atom or a group $NR^1$, CO, $SO_2$ or $CR_2^1$;
a group COCO, $CONR^1$, $COCR_2^1$, $SOCR_2^1$, $SO_2NR^1$, $CR_2^1CR_2^1$, $CR_2^1NR^1$ or $CR_2^1O$;
a group $NR^1CONR^1$, $OCONR^1$, $CONR^1CO$, $CONR^1CR_2^1$, OCOO, $CR_2^1OCR_2^1$, $OCR_2^1CO$, $CR_2^1CONR^1$, $CR_2^1CR_2^1CR_2^1$, $COCR^1R^1CO$, $CR_2^1NR^1CR_2^1$, $CR_2^1SO_2NR^1$, $CR_2^1OCO$ or $NR^1SO_2NR^1$;

where $R^1$ is hydrogen or a $C_{1-6}$-alkyl or alkoxy group optionally substituted by hydroxy, alkoxy, oxa or oxo (e.g. a polyhydroxyalkyl, formyl, acetyl, hydroxyl, alkoxy or hydroxyalkoxy group) and where it is attached to a carbon atom $R^1$ may also be a hydroxyl group.

When X provides a 4–7 atom linkage, conventional linker groups, such as for example those suggested by Justesa in WO-93/10078 or Bracco in U.S. Pat. No. 4,348,377 and WO-94/14478 may be used.

In general such linkages will comprise optionally aza or oxa substituted alkylene chains optionally carring $R^1$ substituents, especially such groups terminating with imine nitrogen or, more preferably, carbonyl carbon atoms, preferbly belonging to iminocarbonyl functional units within the chain. Hydroxylated chains, such as are found in iodixanol are particularly preferred.

Examples of such chains are NCCN, NCCCN, CNCCCNC, and CNCCN, eg.
—NR$^1$COCONR$^1$—
—NR$^1$COCR$^1_2$CONR$^1$—
—NR$^1$CR$^1_2$CR$^1$OHCR$^1_2$NR$^1$—
—CONR$^1$CR$^1_2$CONR$^1$— and
—N(COR$^1$)CR$^1_2$CR$^1$OHN(COR$^1$)—, e.g. as found in iotrolan, iofratol, ioxaglic acid and iodixanol, or as otherwise indicated in WO-94/14478.

Advantageously, in the dimer compounds the X group is not symmetrical. This may be achieved for example by asymmetrical substitution of a symmetrical chain (e.g. N—C—N substituted as NHCONR$^1$) or by selection of an asymmetric chain (e.g. OCN substituted as OCONR$^1$). In particular, it is preferred that the linker group X should be polar and also that it should be hydrophilic.

Thus examples of preferred structures according to the invention include:

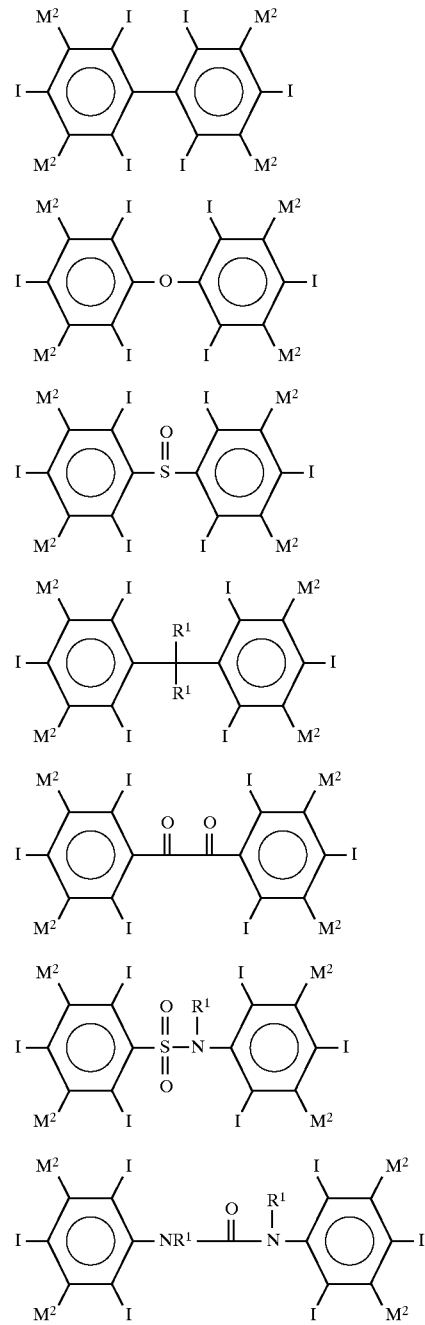
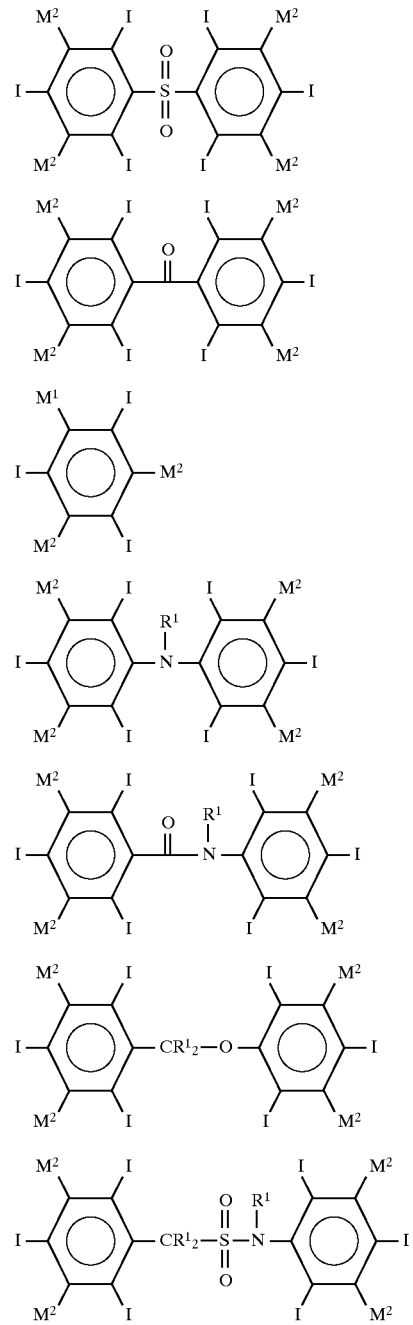

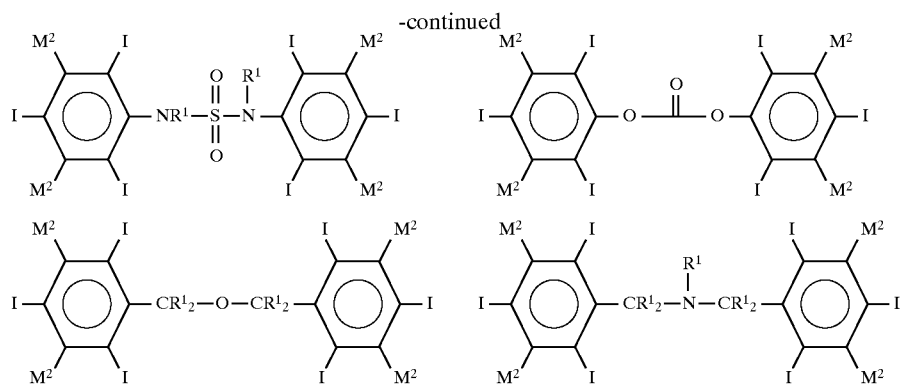

where each $M^2$ is $M_1$ or M, at least one in each compound (and preferably on each ring) being $M_1$, especially where at least one $M^2$ is a $C_{1-4}$-alkyl group substituted by 1, 2, 3 or 4 hydroxy groups (e.g. hydroxymethyl, 2-hydroxyethyl, 2,3-bishydroxy-propyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$), e.g. a hydroxyalkyl or hydroxyalkylcarbonyl group, in particular a hydroxymethyl, hydroxymethylcarbonyl, 2-hydroxyethyl or 2-hydroxyethylcarbonyl group, and where $R^1$ is hydrogen, hydroxyl, hydroxyalkyl (e.g. 2-hydroxyethyl), acetyl or hydroxyalkylcarbonyl.

Particular preferred compounds are those of formula

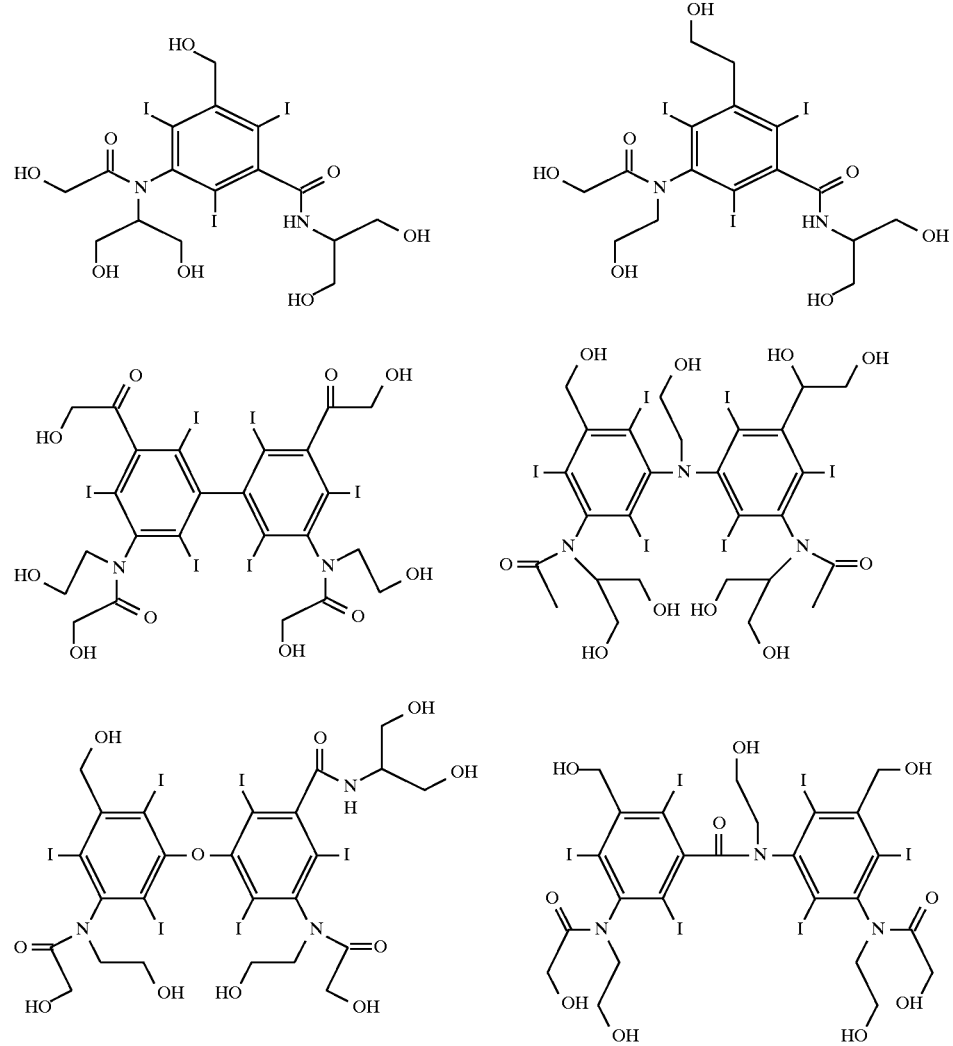

-continued

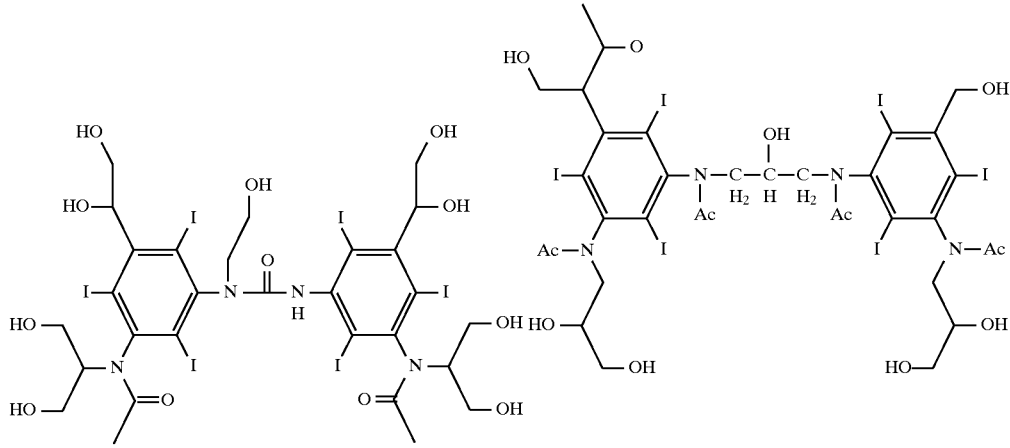

The compounds of the invention may in general be prepared in two or three stages: (a) dimer formation (where necessary), (b) iodination of phenyl groups and (c) substitution of phenyl groups and/or optionally linker moieties by solubilizing moieties.

While, in theory, stages (a), (b) and (c) can be performed in any order, it will generally be preferred to perform the dimer formation step before the iodination step and, for reasons of economy, it will be preferred to perform the iodination step at as late a stage in the synthesis as is feasible so as to reduce iodine wastage. The dimer formation stage may itself be a multi-step procedure with an appropriate activated linker first being attached to one monomer before the resulting linker-monomer conjugate is reacted with a second monomer. Alternatively, dimer formation may be by way of reaction of similarly or cooperatively substituted monomers with the conjugation of the monomers leading to dimer formation.

Where desired the linker group X may be produced by modification, e.g. substitution, oxidation or reduction, of a precursor linker, e.g. in a precursor monomer.

For the monomer compounds, especially those where ring substitution is asymmetric, iodine loading will generally be effected before or after partial substitution of the phenyl ring with R groups.

In all cases, conventional synthetic routes wellknown in the literature (eg methods analogous to those used and described for the production of the compounds referred to in WO-94/14478) may be used.

The compounds of the invention may be used as X-ray contrast agents and to this end they may be formulated with conventional carriers and excipients to produce diagnostic contrast media.

Thus viewed from a further aspect the invention provides a diagnostic composition comprising a compound of formula I (as defined above) together with at least one physiologically tolerable carrier or excipient, e.g. in aqueous solution in water for injections optionally together with added plasma ions or dissolved oxygen.

The contrast agent compositions of the invention may be at ready-to-use concentrations or may be formulated in concentrate form for dilution prior to administration. Generally compositions in ready-to-use form will have iodine concentrations of at least 100 mgI/ml, preferably at least 150 mgI/ml, with concentrations of at least 300 mgI/ml, e.g. 320 to 400 mgI/ml being generally preferred. The higher the iodine concentration the higher the diagnostic value but equally the higher the solution's viscosity and osmolality. Normally the maximum iodine concentration for a given compound will be determined by its solubility, and by the upper tolerable limits for viscosity and osmolality.

For contrast media which are administered by injection, the desirable upper limit for solution viscosity at ambient temperature (20° C.) is 30 mPas; however viscosities of up to 50 or even up to 60 mPas can be tolerated although their use in paediatric radiography will then generally be contraindicated. For contrast media which are to be given by bolus injection, e.g. in angiographic procedures, osmotoxic effects must be considered and preferably osmolality should be below 1 Osm/kg $H_2O$, especially below 850 mOsm/kg $H_2O$, in particular within 50 or less, preferably within 10, mOsm of isotonicity (about 300 mOsm/kg $H_2O$).

With the compounds of the invention, such viscosity, osmolality and iodine concentration targets can readily be met. Indeed effective iodine concentrations may be reached with hypotonic solutions. It may thus be desirable to make up solution tonicity by the addition of plasma cations so as to reduce the toxicity contribution which derives from ionic imbalance effects following bolus injection. Such cations will desirably be included in the ranges suggested in WO-90/01194 and WO-91/13636.

Preferred plasma cation contents for the contrast media of the invention, especially contrast media for angiography, are as follows:

| | |
|---|---|
| sodium | 2 to 100, especially 15 to 75, particularly 20 to 70, more particularly 25 to 35 mM |
| calcium | up to 3.0, preferably 0.05 to 1.6, especially 0.1 to 1.2, particularly 0.15 to 0.7 mM |
| potassium | up to 2, preferably 0.2 to 1.5, especially 0.3 to 1.2, particularly 0.4 to 0.9 mM |
| magnesium | up to 0.8, preferably 0.05 to 0.6, especially 0.1 to 0.5, particularly 0.1 to 0.25 mM |

The plasma cations may be presented, in whole or in part, as counterions in ionic contrast agents. Otherwise they will generally be provided in the form of salts with physiologically tolerable counteranions, e.g. chloride, sulphate, phosphate, hydrogen carbonate, etc., with plasma anions especially preferably being used.

Besides plasma cations, the contrast media may contain other counterions where the dimer is ionic and such counterions will of course preferably be physiologically tolerable. Examples of such ions include alkali and alkaline earth metal ions, ammonium, meglumine, ethanolamine, diethanolamine, chloride, phosphate, and hydrogen carbonate. Other counterions conventional in pharmaceutical formulation may also be used. The compositions moreover may contain further components conventional in X-ray contrast media, e.g. buffers, etc.

Publications referred to herein are incorporated herein by reference.

The invention will now be described further with reference to the following non-limiting Examples.

EXAMPLE 1

1,3,5-Triiodo-2,4-di(1,2,3-trihydroxy-1-propyl)-6-(3-hydroxy-1-propen-1-yl)benzene.

a. 1,3,5-Triiodo-2,4,6-trimethylbenzene

Iodine (19.0 g, 75 mmol) was dissolved in carbon tetrachloride (75 ml). Mesitylene (7.0 ml, 50 mmol) and bis(trifluoroacetoxy)phenyl iodide (35.5 g, 82 mmol) were added and the solution was stirred at ambient temperature for 2 hours. The precipitate, which was collected by filtration, was washed with cold carbon tetrachloride and dried. Yield: 20.5 g (82%).

$^1$H NMR (CDCl$_3$): 3.31 (s).

b. 1,3,5-Triiodo-2,4,6-triacetoxymethylbenzene

Triiodomesitylene (19.5 g, 39 mmol) was added to glacial acetic acid (200 ml) containing acetic anhydride (400 ml) and concentrated sulfuric acid (40 ml). Solid potassium permanganate (24.6 g, 156 mmol) was then added in small portions over a period of 3 h. After stirring for 16 h, the solvent was evaporated and water (200 ml) was added. The aqueous suspension was extracted with dichloromethane (250 ml) and the organic phase was washed with water (3×50 ml), dried (MgSO$_4$) and evaporated. The solid residue was suspended in acetone and the white crystalline product was collected by filtration. Yield: 9.3 g (35%).

$^1$H NMR (CDCl$_3$): 5.66 (s, 6H), 2.20 (s, 9H).

c. 1,3,5-Triiodo-2,4,6-trihydroxymethylbenzene 1,3,5-Triiodo-2,4,6-triacetoxymethylbenzene (9.3 g, 13.8 mmol) was suspended in methanol (120 ml) and K$_2$CO$_3$ (0.32 g, 2.3 mmol) was added. The mixture was stirred at ambient temperature for 16 h, and , after neutralization of the solution with 2M aqueous HCl, the organic solvent was evaporated. The residue was suspended in water and the white solid was collected by filtration and washed with water, methanol and ether. Yield: 7.1 g (94%).

$^1$H NMR (DMSO-d$_6$): 5.08 (s, 6H), 3.35 (br s, 3H)

d. 1,3,5-Triiodobenzene-2,4,6-trialdehyde 1,3,5-Triiodo-2,4,6-trihydroxymethylbenzene (4.5 g, 8.2 mmol) was dissolved in DMSO (80 ml). Triethylamine (51.7 ml, 371 mmol) and pyridine.SO$_3$ (11.8 g, 74.2 mmol) were added and the mixture was stirred for two hours. The two phases were separated and the lower phase was cooled to 0° C., poured into water (150 ml) and stirred for 30 min at 0° C. The white solid was collected by filtration, washed with water and dried. Yield: 3.0 g (67%).

$^1$H NMR (DMSO-d$_6$): 9.64 (s).

e. 1,3,5-Triiodo-2,4,6-tris(2-prop-1-enoic acid)benzene methyl ester

Sodium hydride (194 mg 80% in mineral oil, 6.5 mmol) was dissolved in DMSO (13 ml) and triethylphosphonoacetate (1.16 ml, 5.80 mmol) was added. After stirring the solution for 30 min, 1,3,5-triiodobenzene-2,4,6-trialdehyde (700 mg, 1.30 mmol) was added and the reaction mixture was stirred for 16 h. Water (200 ml) was then added and the pH was adjusted to 1 with 2M aqueous HCl. The slurry was extracted with dichloromethane (2×200 ml) and the combined organic phases were washed with water (3×50 ml), dried (MgSO$_4$) and evaporated. Purification by column chromatography (silica gel CH$_2$Cl$_2$-methanol 99:1) gave the pure product as a white solid. Yield: 426 mg (44%).

$^1$H NMR (CDCl$_3$): 7.48 (d, 3H, J 16.2 Hz), 5.95 (d, 3H, J 16.2 Hz), 4.30 (q, 6H, J 7.2 Hz), 1.36 (t, 9H, J 7.2 Hz).

f. 1,3,5-Triiodo-2,4,6-tris(1-hydroxyprop-en-3-yl)benzene 1,3,5-Triiodo-2,4,6-tris(2-prop-1-enoic acid)benzene methyl ester (650 mg, 0.87 mmol) was dissolved in toluene (10 ml) and diisobutylaluminium hydride (5.44 ml of a 1.2M solution in toluene) was added at 0° C. After stirring for 40 min at 0° C., the solution was poured into methanol (50 ml) and the resulting slurry was stirred for another 45 min. The solids were filtered off and the solution was evaporated giving a white solid residue which was purified by trituration with diethyl ether. Yield: 510 mg (94%).

$^1$H NMR (CD$_3$OD): 6.44 (d, 3H, J 16.0 Hz), 5.57 (dt, 3H, J$_d$ 16.0 Hz, J$_t$ 5.8 Hz), 4.23 (m, 6H).

g. 1,3,5-Triiodo-2,4,6-tris(1-acetoxyprop-en-3-yl)benzene 1,3,5-Triiodo-2,4,6-tris(1-hydroxyprop-en-3-yl)benzene (560 mg, 0.90 mmol) was dissolved in a mixture of pyridine (8 ml) and acetic anhydride (8 ml). After stirring at ambient temperature for 16 hours, the solvent was evaporated and the residue was purified by preparative HPLC (RP-18, CH$_3$CN: H$_2$O 80:20). Yield 310 mg (46%).

$^1$H NMR (CDCl$_3$): 6.46 (dt, 3H, J$_d$ 16.2 Hz, J$_t$ 1.6 Hz), 5.68 (dt, 3H, J$_d$ 16.2 Hz, J$_t$ 5.6 Hz), 4.83 (dd, 6H, J$_1$ 5.6 Hz, J$_2$ 1.6 Hz), 2.12 (s, 9H).

$^{13}$CNMR (CDCl$_3$): 170.6, 146.3, 140.9, 131.5, 98.7, 63.5, 20.9.

h. 1,3,5-Triiodo-2,4-di(1,2,3-trihydroxy-1-propyl)-6-(3-hydroxy-1-propen-1-yl)benzene 1,3,5-Triiodo-2,4,6-tris(1-acetoxyprop-en-3-yl)benzene (100 mg, 0.133 mmol) was dissolved in formic acid (5 ml) containing hydrogen peroxide (0.054 ml). The mixture was stirred at ambient temperature for 21 hours and the solvent was evaporated. Methanol (5 ml) was added followed by solid K$_2$CO$_3$ (195 mg), and, after stirring for 1 hour, the solvent was evaporated. The product was purified by preparative HPLC (CH$_3$CN: H$_2$O 3:97).

$^1$H NMR (D$_2$O): 6.45 (d, 1H, J 16.0 Hz), 5.40–5.55 (m, 1H), 4.54–4.90 (m, 11H), 4.23–4.31 (m, 2H), 3.62–3.91 (m, 4H). MS (ESP): 692 (M$^+$).

EXAMPLE 2

1,3,5-Triiodo-2,4,6-tri(1,2,3-trihydroxy-1-propyl) benzene.

1,3,5-Triiodo-2,4,6-tris(1-acetoxyprop-en-3-yl)benzene (100 mg, 0.133 mmol, from Example 1g) was dissolved in formic acid (5 ml) containing hydrogen peroxide (0.081 ml). The mixture was stirred at room temperature for 40 hours and the solvent was evaporated. Methanol (5 ml) was added followed by solid K$_2$CO$_3$ (195 mg), an, after stirring for 1 h, the solvent was evaporated. The product was purified by preparative HPLC (CH$_3$CN:H$_2$O 3:97).

$^1$H NMR (CD$_3$OD): 4.57–4.94 (m, 15H), 3.62–3.99 (m, 6H). MS (ESP): 744 (M+18).

EXAMPLE 3

N-Acetyl-3-hydroxymethyl-5-(2,3-dihydroxypropylaminocarbonyl)-N-(2,3-dihydroxypropyl)-2,4,6-triiodoaniline a. 1-Hydroxymethyl-3-nitro-5-benzoic acid methyl ester 1-Nitroisophthalic acid monomethyl ester (22.5 g, 100 mmol) was dissolved in dry THF (675 ml) and BF$_3$•Et$_2$O (25.2 ml, 200 mmol) was added. NaBH$_4$ (5.1 g, 135 mmol) was then added portionwise during 1 h. After stirring for 2 additional h, ethanol (20 ml) was added slowly followed by water (200 ml) and diethyl ether (400 ml). The phases were separated and the aqueous phase was extracted once with diethyl ether (100 ml). The combined organic phases were washed with a saturated aqueous solution of NaHCO$_3$, dried (Na$_2$SO$_4$) and evaporated. Yield: 20 g (96%). HPLC analysis indicated >95% purity of the product.

$^1$H NMR (CDCl$_3$): 8.72 (s, 1H), 8.42 (s, 1H), 8.32 (s, 1H), 4.86 (s, 2H), 3.97 (s, 3H), 2.37 (br s, 1H).

b. 1-Hydroxymethyl-3-nitro-5-(2,3-dihydroxy propylaminocarbonyl)benzene

The methyl ester from Example 3a (20.5 g, 97 mmol) was mixed with 2,3-dihydroxypropylamine (9.6 g, 106 mmol) and the mixture was heated to 90° C. After 45 min, the pressure was reduced to 200 mm Hg and heating was continued for 2 h. The crude product, which was >95% pure according to HPLC analysis, was used without further purification in the next step. Yield: 22.8 g (87%).

$^1$H NMR (CD$_3$OD): 8.57 (s, 1H), 8.38 (s, 1H), 8.19 (s, 1H), 4.77 (s, 2H), 3.81–3.88 (m, 1H), 3.39–3.63 (m, 4H).

c. 3-Hydroxymethyl-5-(2,3-dihydroxypropylamino carbonyl)aniline

1-Hydroxymethyl-3-nitro-5-(2,3-dihydroxypropylaminocarbonyl)benzene (12.0 g, 44.4 mmol) was hydrogenated in methanol (150 ml) at 60 psi H$_2$ using Pd/C (10%, 100 mg) as the catalyst. The catalyst was removed by filtration and the residue was evaporated. Addition of methanol (10 ml) precipitated the product as a white solid which was filtered off and dried. Yield: 6.6 g (62%).

$^1$H NMR (CD$_3$OD): 7.05–7.09 (m, 1H), 6.98–7.03 (m, 1H), 6.83–6.87 (m, 1H), 4.53 (s, 2H), 3.77–3.85 (m, 1H), 3.8–3.59 (m, 4H), 3.32–3.42 (m, 1H).

MS (ESP, m/e): 241 ([M+1]$^+$, 100%).

d. 3-Hydroxymethyl-5-(2,3-dihydroxypropylamino carbonyl)-2,4,6-triiodoaniline

3-Hydroxymethyl-5-(2,3-dihydroxypropyl aminocarbonyl)aniline (500 mg, 2.1 mmol) was dissolved in water (175 ml) and an aqueous solution of KICl$_2$ (70%, w/w) was added in portions of 0.1 ml during 8 h. A total amount of 1.0 ml KICl$_2$ solution was added. After a total reaction time of 6 h, the solution was extracted with ethyl acetate (1000 ml) which was separated and washed with an aqueous solution of Na$_2$S$_2$O$_3$ (0.2M, 100 ml). Evaporation followed by purification by preparative HPLC gave 432 mg (33%) of the pure product.

$^1$H NMR (CD$_3$OD): 5.10 (s, 2H), 3.90–3.98 (m, 1H), 3.72 (ddd, J$_1$=0.7 Hz, J$_2$=4.2 Hz, J$_3$=11.4 Hz), 1H), 3.60 (dd, J$_1$=6.0 Hz, J$_2$=11.4 Hz, 1H), 3.49 (ddd, J$_1$=1.2 Hz, J$_2$=6.0 Hz, J$_3$=13.5 Hz, 1H), 3.37 (ddd, J$_1$=1.2 Hz, J$_2$=6.1 Hz, J$_3$=13.2 Hz, 1H), 2.62 (s, 1H), 2.28 and 2.34 (2s, 2H).

MS (ESP, m/e): 618 (M$^+$, 100%), 640 ([M+Na]$^+$, 55%).

e. N-acetyl-3-acetoxymethyl-5-(2,3-diacetoxy propylaminocarbonyl)-2,4,6-triiodoaniline 3-Hydroxymethyl-5-(2,3-dihydroxypropyl aminocarbonyl)-2,4,6-triiodoaniline (3.3 g, 5.3 mmol) was suspended in glacial acetic acid (12 ml) containing acetic anhydride (48 ml) and concentrated sulfuric acid (0.08 ml). The mixture was stirred at 60° C. for 3 h, allowed to cool to room temperature, and CH$_2$Cl$_2$ (100 ml) and water (100 ml) were added. The organic phase was washed with water (3×50 ml) and a saturated aqueous solution of NaHCO$_3$ (2×50 ml). After drying (MgSO$_4$) and evaporation, the residue was dissolved in a mixture of CH$_2$Cl$_2$ and methanol (9:1) and filtered through a short silica pad and evaporated. Yield: 3.0 g (71%).

$^1$H NMR (CDCl$_3$): 8.27–8.32 (m, 1H), 5.51 (s, 2H), 5.18–5.22 (m, 1H), 4.17–4.42 (m, 2H), 3.67–3.84 (m, 1H), 3.41–3.60 (m, 1H), 2.56 (s, 3H), 2.04–2.14 (8s, 12H).

MS (ESP, m/e): 786 (M$^+$, 100%), 809 ([M+Na]$^+$, 81%).

f. N-Acetyl-3-hydroxymethyl-5-(2,3-dihydroxy propylaminocarbonyl)-N-(2,3-dihydroxypropyl)-2,4,6-triiodoaniline N-acetyl-3-acetoxymethyl-5-(2,3-diacet oxypropylaminocarbonyl)-2,4,6-triiodoaniline (1.0 g, 1.27 mmol) was suspended in a mixture of methanol (6 ml) and water (30 ml) and pH was adjusted to 12.0 using a 2M aqueous solution of NaOH. After stirring for 1 h, 1-bromo-2,3-propanediol (0.99 g, 6.4 mmol) was added and the pH was adjusted to 11.6 using a 2M aqueous solution of HCl. 1-Bromo-2,3-propanediol (0.99 g, 6.4 mmol) was again added after 16 and 18 h and after 24 h, pH was adjusted to 6.5 using a 2M aqueous solution of HCl. After evaporation, the residue was purified by preparative HPLC. Yield: 0.373 g (40%).

$^1$H NMR (D$_2$O): 5.20 (s, 2H), 3.23–3.99 (m, 12H), 1.79 (2s, 3H).

MS (ESP, m/e): 734 (M$^+$, 60%), 756 ([M+Na]$^+$, 100%).

EXAMPLE 4

N,N'-bis(hydroxyacetyl)-3,5-diamino-2,4,6-triiodobenzylalcohol a. 3,5-Diaminobenzylalcohol A solution of 3,5-dinitrobenzylalcohol (2.20 g, 11.1 mmol) in methanol (90 ml) and a Pd/C catalyst (10%, 100 mg) was hydrogenated in a Parr apparatus at 60 psi. The solution was filtered and the solvent was removed by evaporation. The crude product was used without purification in the next step.

$^1$H NMR (CDCl$_3$): 6.12–6.14 (m, 2H), 5.96–5.98 (m, 1H), 4.51 (s, 2H), 3.60 (br s, 4H).

b. 3,5-Diamino-2,4,6-triiodobenzylalcohol

The crude product from the previous example dissolved in a mixture of methanol (310 ml) and water (60 ml) and pH was adjusted to 1.5 using a 4M aqueous solution of HCl. A solution of KICl$_2$ (70%, 11.2 g) was added dropwise at such a rate, that the color disappeared between each addition. After stirring for 5 additional min, the precipitate was filtered off and washed with water (3×50 ml), ether (3×50 ml) and dried. Yield: 4.50 g (80%).

$^1$H NMR (DMSO-d$_6$): 5.20 (s, 4H), 4.81–4.94 (m, 3H).

c. 3,5-Diamino-2,4,6-triiodobenzylacetate 3,5-Diamino-2,4,6-triiodobenzylalcohol (4.42 g, 8.56 mmol) was dissolved in a mixture of pyridine (50 ml) and acetic anhydride (2.5 ml) and the mixture was stirred at room temperature for 16 h. The solvents were evaporated and the residue was washed with ether (3×50 ml), water (3×50 ml) and dried. Yield: 4.52 g (95%).

$^1$H NMR (DMSO-d$_6$): 5.35 (s, 2H), 5.28 (s, 4H), 2.04 (s, 3H).

$^{13}$C NMR (DMSO-d$_6$): 170.5, 148.1, 139.0, 78.0, 73.6, 70.0, 20.8.

d. 3,5-Bis(acetoxyacetylamino)-2,4,6-triiodobenzylacetate 3,5-Diamino-2,4,6-triiodobenzylacetate (5.58 g, 10 mmol) was mixed with acetoxyacetyl chloride (3.22 ml, 30 mmol) and dimethylacetamide (50 ml) and the mixture was stirred for 17 h. Ether (600 ml) was added, and after 20 min, the precipitate was collected, washed with water (3×50 ml) and dried. Recrystallization from acetonitrile gave 3.3 g (44%) of the pure product.

$^1$H NMR (DMSO-d$_6$): 10.27 and 10.19 (2s, 2:1, 2H), 5.51 (s, 2H), 4.66 (s, 4H), 2.13 (s, 3H), 2.12 (s, 3H), 2.06 (s, 3H).

e. N,N'-bis(hydroxyacetyl)-3,5-diamino-2,4,6-triiodobenzylalcohol 3,5-Bis(acetoxyacetylamino)-2,4,6-triiodobenzylacetate (152 mg, 0.2 mmol) was dissolved in a mixture of methanol (6 ml) and 1M aqueous NaOH (2 ml) and the solution was stirred for 2 h at room temperature. After neutralization with 1M HCl, the solvents were removed by evaporation and the product was purified by preparative HPLC. Yield: 105 mg (83%).

MS (ESP, m/e): 655 ([M+Na]$^+$, 100%).

EXAMPLE 5

N,N'-Bis(hydroxyacetyl)-N-(2-hydroxyethyl)-3,5-diamino-2,4,6-triiodobenzylalcohol a. N,N'-Bis(acetoxyacetyl)-N-(2-acetoxyethyl)-3,5-diamino-2,4,6-triiodobenzylacetate 3,5-Bis(acetoxyacetylamino)-2,4,6-triiodobenzylacetate (2.15 g, 2.84 mmol) was dissolved in a mixture of DMSO (5 ml) and dimethylacetamide (5 ml) containing $Cs_2CO_3$ (1.0 g, 3.07 mmol) and 2-bromoethyl acetate (0.31 ml, 2.84 ml). The mixture was stirred at room temperature for 48 h, ether (100 ml) and aqueous $NaH_2PO_4$ buffer were added and the organic phase was washed with water and dried. Purification by preparative HPLC gave 520 mg (22%) of the product.

$^1$H NMR (CDCl$_3$): 7.86 (s, 1H), 5.66 (s, 2H), 4.80 (s, 2H), 3.81–4.44 (m, 6H), 2.13–2.27 (m, 12H).

MS (ESP, m/e): 845 ([M+1]$^+$, 100%), 866 ([M+Na]$^+$, 24%).

b. N,N'-Bis(hydroxyacetyl)-N-(2-hydroxyethyl)-3,5-diamino-2,4,6-triiodobenzylalcohol N,N'-Bis(acetoxyacetyl)-N-(2-acetoxyethyl)-3,5-diamino-2,4,6-triiodobenzylacetate (0.50 g, 0.59 mmol) was dissolved in a mixture of methanol (5 ml), water (5 ml) and aqueous 1M NaOH (1 ml). The solution was stirred for 2 h, pH was adjusted to 2 using aqueous HCl and the product was purified by preparative HPLC. Yield: 240 mg (67%).

$^1$H NMR DMSO-d$_6$): 9.85 (br s, 1H), 5.77 (br s, 1H), 4.79–5.26 (m, 3H), 3.20–3.71 (m, 6H). MS (ESP, m/e): 676 (M$^+$, 57%), 698 ([M+Na]$^+$, 100%).

EXAMPLE 6

N,N'-Bis(hydroxyacetyl)-N,N'-bis(2-hydroxyethyl)-3,5-diamino-2,4,6-triiodobenzylalcohol

3,5-Bis(acetoxyacetylamino)-2,4,6-triiodobenzylacetate (190 mg, 0.25 mmol), prepared according to Example 4, was dissolved in dimethylacetamide (5 ml) under an argon atmosphere. 2-Bromoethyl acetate (0.22 ml, 2.0 mmol) and $K_2CO_3$ (138 mg, 1.0 mmol) were added. After 16 h, DMSO (1.5 ml), 2-bromoethyl acetate (0.22 ml, 2.0 mmol) and $K_2CO_3$ (138 mg, 1.0 mmol) were added and the suspension was stirred for another 24 h. Aqueous $NaH_2PO_4$ was added and the resulting solution was extracted with ether (3×25 ml). The combined organic phases were washed with water (4×20 ml) and then dried (MgSO$_4$). The solvent was removed by evaporation and the residue, a colorless oil, was dissolved in a mixture of methanol (3 ml) an 1M aqueous NaOH (3 ml). The solution was stirred for 1 h, pH was adjusted to 6 using aqueous HCl and the solvents were removed by evaporation. Purification by preparative HPLC gave 60 mg (33%) of the product.

MS (ESP, m/e): 720 (M$^+$, 100%), 742 ([M+Na]$^+$, 36%).

EXAMPLE 7

N,N'-Bis(hydroxyacetyl)-N-(2,3-dihydroxypropyl)-3,5-diamino-2,4,6-triiodobenzylalcohol a. N,N'-Bis(acetoxyacetyl)-N-[(2,2-dimethyl-1,3-dioxolane-4-yl)-methyl]-3,5-diamino-2,4,6-triiodobenzylacetate 3,5-Bis(acetoxyacetylamino)-2,4,6-triiodobenzylacetate (90 mg, 0.12 mmol), prepared according to Example 4, was dissolved in a mixture of dimethylacetamide (3 ml) and DMSO (3 ml). 4-Bromomethyl-2,2-dimethyl-1,3-dioxolane (0.097 g, 0.5 mmol) and $Cs_2CO_3$ (0.10 g, 0.3 mmol) were added and the solution was stirred at room temperature for 48 h. Aqueous $NaH_2PO_4$ was added and the solution was extracted with ether (3×25 ml). The combined organic phases were washed with water (3×15 ml), dried (MgSO$_4$) and evaporated. Purification by preparative HPLC gave 36 mg (35%) of the pure product.

$^1$H NMR (DMSO-d$_6$): 10.30 (br s, 1H), 5.53 (s, 2H), 3.61–4.68 (m, 9H), 2.13 (s, 3H), 2.07 (s, 3H), 2.06 (s, 3H), 1.17–1.34 (m, 6H).

MS (ESP, m/e): 894 ([M+Na]$^+$, 100%), 910 ([M+K]$^+$, 11%).

b. N,N'-Bis(hydroxyacetyl)-N-(2,3-dihydroxypropyl)-3,5-diamino-2,4,6-triiodobenzylalcohol N,N'-Bis(acetoxyacetyl)-N-[(2,2-dimethyl-1,3-dioxolane-4-yl)-methyl]-3,5-diamino-2,4,6-triiodobenzylacetate (36 mg, 0.042 mmol) was dissolved in a mixture of methanol (3 ml) and water (4 ml) and the pH was adjusted to 12 using a 1M aqueous solution of NaOH. After stirring for 2 h, pH was adjusted to 1 using 1M aqueous HCl and stirring was continued for 16 h. The solution was neutralized with an aqueous $NaH_2PO_4$ buffer, the solvents were removed by evaporation and the residue was purified by preparative HPLC to give 24 mg (81%) of the pure product.

MS (ESP, m/e): 704 (M$^+$, 100%), 726 ([M+Na]$^+$, 34%).

EXAMPLE 8

N,N'-Bis(2-hydroxypropionyl)-3,5-diamino-2,4,6-triiodobenzylalcohol a. N,N'-Bis(2-acetoxypropionyl)-3,5-diamino-2,4,6-triiodobenzylacetate 3,5-Diamino-2,4,6-triiodobenzylacetate (2.79 g, 5.0 mmol) was dissolved in dimethylacetamide (25 ml) and cooled to 0° C. 2-Acetoxypropionyl chloride (3.73 g, 25 mmol) was added dropwise and the mixture was stirred at room temperature for 17 h. The solvents were evaporated and the residue was triturated with diethyl ether. The solid residue was then purified by flash chromatography on silica gel using a mixture of $CH_2Cl_2$ and acetonitrile (5:1) as the eluent. Yield: 2.21 g (56%).

$^1$H NMR (DMSO-d$_6$): 10.20–10.23 (m, 2H), 5.52 (s, 2H), 5.21–5.24 (m, 2H), 2.06–2.13 (m, 9H), 1.51 (d, J=6.9 Hz, 6H).

b. N,N'-Bis(2-hydroxypropionyl)-3,5-diamino-2,4,6-triiodobenzylalcohol

N,N'-Bis(2-acetoxypropionyl)-3,5-diamino-2,4,6-triiodobenzylacetate (0.16 g, 0.2 mmol) was dissolved in a mixture of methanol (5 ml) and water (5 ml) and the pH was adjusted to 12 using a 1M aqueous solution of NaOH. After stirring for 15 h, the solution was neutralized with 1M HCl and the solvents were removed by evaporation. Purification by preparative HPLC gave 61 mg (46%) of the pure product.

MS (ESP, m/e): 660 (M$^+$, 5%), 682 ([M+Na]$^+$, 100%), 698 ([M+K]$^+$, 17%).

EXAMPLE 9

N,N'-Bis(2-hydroxypropionyl)-N-(2-hydroxyethyl)-3,5-diamino-2,4,6-triiodobenzylalcohol a. N,N'-Bis(2-acetoxypropionyl)-N-(2-acetoxyethyl)-3,5-diamino-2,4,6-triiodobenzylacetate N,N'-Bis(2-acetoxypropionyl)-3,5-diamino-2,4,6-triiodobenzylacetate (393 mg, 0.50 mmol) was dissolved in a mixture of dimethylacetamide (4 ml) and DMSO (4 ml) containing 2-bromoethyl acetate (0.083 g, 0.50 mmol) and $Cs_2CO_3$ (244 mg, 0.75 mmol). The mixture was stirred for 17 h, water (20 ml) was added and the mixture was extracted with ether (3×25 ml). The combined organic phases were washed with water (3×20 ml), dried ($MgSO_4$) and evaporated. The residue was purified by preparative HPLC to give 80 mg (18%) of pure product.

$^1$H NMR ($CD_3OD$): 5.72–5.82 (m, 2H), 5.20–5.42 (m, 2H), 3.55–4.48 (m, 4H), 1.90–2.24 (m, 12H), 1.66 (d, J=7.1 Hz, 6H).

MS (ESP, m/e): 1004 ([M+Cs]$^+$, 100%).

b. N,N'-Bis(2-hydroxypropionyl)-N-(2-hydroxyethyl)-3,5-diamino-2,4,6-triiodobenzylalcohol N,N'-Bis(2-acetoxypropionyl)-N-(2-acetoxyethyl)-3,5-diamino-2,4,6-triiodobenzylacetate (120 mg, 0.14 mmol) was dissolved in a mixture of water (7 ml) and methanol (7 ml) and pH was adjusted to 12 using an 1M aqueous solution of NaOH. The mixture was stirred for 2 h, pH was adjusted to 7 with aqueous HCl and the solvents were evaporated. The product was purified by preparative HPLC. Yield: 70 mg (72%).

$^1$H NMR ($CD_3OD$): 5.27–5.34 (m, 2H), 4.31–4.41 (m, 1H), 3.82–4.12 (m, 4H), 3.55–3.73 (m, 1H), 1.51–1.60 (m, 3H), 1.23–1.32 (m, 3H).

MS (ESP, m/e): 726 ([M+Na]$^+$, 100%).

EXAMPLE 10

N,N'-Bis(2-hydroxypropionyl)-N,N'-bis(2-hydroxyethyl)-3,5-diamino-2,4,6-triiodobenzylalcohol a. N,N'-Bis(2-acetoxypropionyl)-N,N'-bis(2-acetoxyethyl)-3,5-diamino-2,4,6-triiodobenzylacetate N,N'-Bis(2-acetoxypropionyl)-3,5-diamino-2,4,6-triiodobenzylacetate (197 mg, 0.25 mmol) was dissolved in a mixture of dimethylacetamide (5 ml) and DMSO (1.5 ml) containing 2-bromoethyl acetate (0.11 ml, 1.0 mmol) and $Cs_2CO_3$ (162 mg, 0.50 mmol). The mixture was stirred for 67 h, water (20 ml) was added and the mixture was extracted with ether (2×75 ml). The combined organic phases were washed with water (5×75 ml), dried ($Na_2SO_4$) and evaporated. The residue was purified by preparative HPLC to give 35 mg (15%) of pure product.

$^1$H NMR (DMSO-$d_6$): 5.49–5.73 (m, 2H), 4.97–5.22 (m, 2H), 3.49–4.00 (m, 6H), 1.86–12.08 (m, 15H), 1.09–1.58 (m, 6H).

b. N,N'-Bis(2-hydroxypropionyl)-N,N'-bis(2-hydroxyethyl)-3,5-diamino-2,4,6-triiodobenzylalcohol N,N'-Bis(2-acetoxypropionyl)-N,N'-bis(2-acetoxyethyl)-3,5-diamino-2,4,6-triiodobenzylacetate (175 mg, 0.18 mmol) was dissolved in a mixture of methanol (8 ml) and water (8 ml) and pH was adjusted to 12 with 1M aqueous NaOH. After stirring for 3 h, the solution was neutralized with aqueous HCl. Purification by preparative HPLC gave 50 mg (37%) of the pure product.

$^1$H NMR ($CD_3OD$): 5.26–5.38 (m, 2H), 3.44–4.08 (m, 6H), 1.32–1.59 (m, 6H).

MS (ESP, m/e): 770 ([M+Na]$^+$, 100%).

EXAMPLE 11

N,N'-Bis(2-hydroxypropionyl)-N-(2,3-dihydroxypropyl)-3,5-diamino-2,4,6-triiodobenzylalcohol a. N,N'-Bis(acetoxypropionyl)-N-[(2,2-dimethyl-1,3-dioxolane-4-yl)-methyl]-3,5-diamino-2,4,6-triiodobenzylacetate N,N'-Bis(2-acetoxypropionyl)-3,5-diamino-2,4,6-triiodobenzylacetate (393 mg, 0.50 mmol) was dissolved in a mixture of DMSO (4 ml) and dimethylacetamide (4 ml) containing $Cs_2CO_3$ (1.80 g, 5.52 mmol) and 4-bromomethyl-2,2-dimethyl-1,3-dioxolane (1.0 ml). The mixture was stirred for 7 days and was then worked up analogous to Example 7a. Purification by preparative HPLC gave 115 mg (26%) of the pure product.

$^1$H NMR ($CD_3OD$): 5.61–5.5.75 (m, 2H), 5.03–5.44 (m, 2H), 3.47–4.55 (m, 6H), 1.98–2.23 (m, 9H), 1.30–1.71 (m, 12H).

MS (ESP, m/e): 922 ([M+Na]$^+$, 100%).

b. N,N'-Bis(2-hydroxypropionyl)-N-(2,3-dihydroxypropyl)-3,5-diamino-2,4,6-triiodobenzylalcohol N,N'-Bis(acetoxypropionyl)-N-[(2,2-dimethyl-1,3-dioxolane-4-yl)-methyl]-3,5-diamino-2,4,6-triiodobenzylacetate (115 mg, 0.13 mmol) was dissolved in a mixture of methanol (8 ml) and water (8 ml) and pH was adjusted to 12 with aqueous 1M NaOH. After 2.5 h, pH was adjusted to 1 with 2M aqueous HCl. After stirring for 17 h, the solution was neutralized with an aqueous $NaH_2PO_4$ buffer and the solvents were removed evaporation. Purification by preparative HPLC gave 65 mg (69%) of the pure product.

MS (ESP, m/e): 756 ([M+Na]$^+$, 100%)

EXAMPLE 12

N,N'-Bis(2,3-dihydroxypropionyl)-3,5-diamino-2,4,6-triiodobenzylalcohol a. N,N'-Bis(2,2-dimethyl-1,3-dioxolane-4-carbonyl)-3,5-diamino-2,4,6-triiodobenzylacetate 3,5-Diamino-2,4,6-triiodobenzylacetate (3.54 g, 6.3 mmol) and 2,2-dimethyl-1,3-dioxolane-4-carboxylic acid chloride (3.13 g, 19 mmol) were dissolved in dimethylacetamide (40 ml) and the solution was stirred for 3.5 h. The solvent was removed by evaporation and the residue was treated with an aqueous solution of $NaHCO_3$. The crystalline residue was filtered off, washed with water and dried. Purification by flash chromatography using a mixture of $CH_2Cl_2$ and $CH_3CN$ (3:1) as the eluent gave 1.90 g (37%) of the pure product.

$^1$H NMR (DMSO-$d_6$): 9.93–10.02 (m, 2H), 5.30 (s, 2H), 4.58 (t, J=6.2 Hz, 1H), 4.29 (t, J=7.3 Hz, 1H), 4.10 (t, J=6.1 Hz, 1H), 2.06 (s, 3H), 1.54 (s, 3H), 1.38 (s, 3H).

MS (ESP, m/e): 902 ([M+dimethylacetamide]$^+$, 100%).

b. N,N'-Bis(2,3-dihydroxypropionyl)-3,5-diamino-2,4,6-triiodobenzylalcohol

N,N'-Bis(2,2-dimethyl-1,3-dioxolane-4-carbonyl)-3,5-diamino-2,4,6-triiodobenzylacetate (1.25 g, 1.55 mol) was dissolved in a mixture of water (50 ml), methanol (25 ml) and concentrated HCl (0.5 ml). After stirring for 4 h, the solution was neutralized with aqueous $NaH_2PO_4$ and the solvents were removed by evaporation. The residue was dissolved in water (10 ml) and the pH was adjusted to 12 with aqueous NaOH. After 30 min, the solution was again neutralized and the solvent was evaporated. The product was purified by preparative HPLC. Yield: 483 mg (45%).

$^1$H NMR (9.65–9.83 (m, 2H), 5.77 (s, 2H), 5.20 (s, 1H), 4.95–5.03 (m, 2H), 4.81 (s, 2H), 4.00–4.08 (m, 2H), 3.72–3.82 (m, 2H), 3.50–3.63 (m, 2H).

MS (ESP, m/e): 692 (M$^+$, 62%), 714 ([M+Na]$^+$, 100%).

EXAMPLE 13

N,N'-Bis(2,3-dihydroxypropionyl)-N-(2-hydroxyethyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (204 mg, 0.25 mmol)

was dissolved in a mixture of dimethylacetamide (4 ml) and DMSO (2.5 ml) containing $Cs_2CO_3$ (650 mg, 2.0 mmol) and 2-bromoethyl acetate (0.035 ml, 0.31 mmol). After stirring for 1 week, ether (150 ml) and a $NaH_2PO_4$ buffer (100 ml) were added, the organic phase was separated and the aqueous phase was extracted with ether (150 ml). The combined organic phases were then washed with water (6×100 ml), dried ($Na_2SO_4$) and evaporated. The residue was dissolved in a mixture of methanol (20 ml) and water (20 ml) and pH was adjusted to 12 with aqueous NaOH. After stirring for 1 h, the pH was adjusted to 1.5 with concentrated HCl and stirred for another 16 h. The solution was neutralized with aqueous $NaH_2PO_4$ and the solvents were evaporated. Preparative HPLC gave 55 mg (30%) of the pure product.

MS (ESP, m/e): 736 ($M^+$, 28%), 758 ($[M+Na]^+$, 100%).

EXAMPLE 14

N,N'-Bis(2,3-dihydroxypropionyl)-N,N'-bis(2-hydroxyethyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (204 mg, 0.25 mmol) was dissolved in a mixture of dimethylacetamide (5 ml) and DMSO (1.5 ml) containing $K_2CO_3$ (276 mg, 2.0 mmol) and 2-bromoethyl acetate (0.44 ml, 4.0 mmol). After stirring for 48 h, an aqueous $NaH_2PO_4$ buffer was added and the mixture was extracted with ether (2×150 ml). The combined organic phases were washed with water (6×100 ml), dried ($Na_2SO_4$) and evaporated. The solid residue was dissolved in a mixture of methanol (12 ml) and water (12 ml) and the pH was adjusted to 12 with aqueous NaOH. After stirring for 18 h, the solution was acidified with concentrated HCl (0.70 ml) and stirring was continued for 3 h. The solution was neutralized and the solvents were removed by evaporation. The product was purified by preparative HPLC. Yield: 98 mg (50%).

MS (ESP, m/e): 802 ($[M+Na]^+$n 100%).

EXAMPLE 15

N,N'-Bis(2,3-dihydroxypropionyl)-N-(2,3-dihydroxypropyl)-3,5-diamino-2,4,6-triiodobenzylalcohol N,N'-Bis(2,2-dimethyl-1,3-dioxolane-4-carbonyl)-3,5-diamino-2,4,6-triiodobenzylacetate (408 mg, 0.50 mmol) was dissolved in a mixture of dimethylacetamide (4 ml) and DMSO (4 ml) containing $Cs_2CO_3$ (1.80 g, 5.52 mmol) and 2,2-dimethyl-1,3-dioxolane-4-carboxylic acid chloride (2.0 ml). After stirring for 8 days, aqueous $NaH_2PO_4$ (100 ml) was added and the mixture was extracted with diethyl ether (2×150 ml). The combined organic phases were washed with water (6×100 ml), dried ($Na_2SO_4$) and evaporated. The residue was dissolved in a mixture of methanol (10 ml) and water (10 ml) and pH was adjusted to 12 with aqueous NaOH. After stirring for 2 h, concentrated HCl (1.0 ml) was added and stirring was continued for 16 h. After neutralization, the solvents were evaporated and the residue was purified by preparative HPLC. Yield: 149 mg (39%).

MS (ESP, m/e): 766 ($M^+$, 60%), 788 ($[M+Na]^+$, 100%).

EXAMPLE 16

Oxalic bis[3-hydroxymethyl-5-(2,3-dihydroxypropylaminocarbonyl)-2,4,6-triiodobenzeneamide]

a. 3-Acetoxymethyl-5-(2,3-diacetoxypropylaminocarbonyl)-2,4,6-triiodoaniline

3-Hydroxymethyl-5-(2,3-dihydroxypropylaminocarbonyl)-2,4,6-triiodoaniline (1.89 g, 3.06 mmol) prepared according to Example 3d, was dissolved in a mixture of acetic anhydride (5 ml) and pyridine (5 ml). The mixture was stirred at room temperature for 24 h, $CH_2Cl_2$ (100 ml) was added and the solution was washed with water (3×25 ml), with a saturated aqueous solution of $NaHCO_3$, dried ($Na_2SO_4$) and evaporated. The product was purified by flash chromatography on silica gel using a mixture of $CH_2Cl_2$ and methanol (98:2) as the eluent. Yield: 1.30 g (57%).

$^1$H NMR ($CDCl_3$): 6.10–6.25 (m, 1H), 5.48 (s, 2H), 5.20–528 (m, 1H), 4.22–4.43 (m, 2H), 3.53–3.89 (m, 2H), 2.06–2.13 (m, 9H).

MS (ESP, m/e): 744 ($M^+$, 100%).

b. Oxalic bis[3-hydroxymethyl-5-(2,3-dihydroxypropylaminocarbonyl)-2,4,6-triiodobenzeneamide]

3-Acetoxymethyl-5-(2,3-diacetoxypropylaminocarbonyl)-2,4,6-triiodoaniline (100 mg, 0.134 mmol) was dissolved in dioxane (1.0 ml) and the solution was heated to 90° C. Oxalyl chloride (0.096 mmol) was added and the mixture was stirred at 78° C. for 17 h. After cooling to room temperature, water (1.0 ml) was added and pH was adjusted to 12 with aqueous NaOH. After stirring for 4 h, the solution was neutralized, the solvents were evaporated and the residue was purified by preparative HPLC. Yield: 14 mg (16%).

$^1$H NMR ($CD_3OD$): 5.24 (s, 2H), 3.38–4.03 (m, 10H).

MS (ESP. m/e): 1290 ($M^+$, 33%), 1312 ($[M+Na]^+$, 100%).

EXAMPLE 17

Malonic bis[3-hydroxymethyl-5-(2,3-dihydroxypropylaminocarbonyl)-2,4,6-triiodobenzeneamide]

3-Acetoxymethyl-5-(2,3-diacetoxypropylaminocarbonyl)-2,4,6-triiodoaniline (100 mg, 0.134 mmol) prepared according to Example 16a, was dissolved in dioxane (1.0 ml) and malonyl chloride (0.097 mmol) was added. The mixture was stirred at 90° C. for 2 h and the solution was allowed to cool to room temperature. Water (1 ml) was added and pH was adjusted to 12 with aqueous NaOH. After stirring at 60° C. for 18 h, the solution was neutralized and the solvents were evaporated. The product was purified by preparative HPLC. Yield: 34 mg (39%).

MS (ESP, m/e): 1304 ($M^+$, 68%), 1326 ($[M+Na]^+$, 100%).

EXAMPLE 18

N,N'-diacetyl-N,N'-bis[3-hydroxymethyl-5-(2,3-dihydroxypropylaminocarbonyl)-2,4,6-triiodophenyl]-1,3-diamino-2-hydroxypropane N-acetyl-3-acetoxymethyl-5-(2,3-acetoxypropylaminocarbonyl)-2,4,6-triiodoaniline (300 mg, 0.38 mmol) prepared according to Example 3e was dissolved in a mixture of water (1.2 ml) and methanol (0.2 ml) and pH was adjusted to 12 with aqueous NaOH. Epichorohydrine (0.28 mmol) was added and the mixture was stirred at room temperature for 65 h. The solution was neutralized and the product was isolated by preparative HPLC. Yield: 60 mg (20%).

MS (ESP, m/e): 1398 ($[M+Na]^+$, 100%).

EXAMPLE 19

N-[3-hydroxymethyl-5-(2,3-dihydroxypropylaminocarbonyl)-2,4,6-triiodophenyl]-N'[3,5-bis(2,3-dihydroxypropylaminocarbonyl)-2,4,6-triiodophenyl]urea a. N-[3-acetoxymethyl-5-(2,3-diacetoxypropyl aminocarbonyl)-2,4,6-triiodophenyl]-N'[3,5-bis(2,3-dihacetoxypropylaminocarbonyl)-2,4,6-triiodophenyl]urea 3,5-Bis(2,3-diacetoxypropylaminocarbonyl)-2,4,6-triiodoaniline (260 mg, 0.30 mmol) was dissolved in dioxane (1.0 ml) and a solution of phosgene in toluene (1.93M, 1.8 ml) was added. The flask was tightly sealed and then heated to 60° C. for 17 h. After cooling to room temperature, the solvent was distilled off at reduced pressure. Dioxane (3 ml) was added and distilled off again. This procedure was repeated twice. Dioxane (1 ml) was added followed by 3-acetoxymethyl-5-(2,3-diacetoxypropylaminocarbonyl)-2,4,6-triiodoaniline (0.245 g, 0.31 mmol), prepared according to Example 16a, and Hg(OCOCF$_3$)$_2$ (20 mg). The mixture was stirred for 16 h at room temperature, the solvent was evaporated and the residue was purified by preparative HPLC. Yield: 0.192 g (39%).

MS (ESP, m/e): 1643 (M$^+$, 100%), 1665 ([M+Na]$^+$, 34%).

b. N-[3-hydroxymethyl-5-(2,3-dihydroxypropyl aminocarbonyl)-2,4,6-triiodophenyl]-N'[3,5-bis(2,3-dihydroxypropylaminocarbonyl)-2,4,6-triiodophenyl]urea The product from Example 19a was dissolved in a mixture of methanol (5 ml) and water (5 ml) and the pH was adjusted to 12 using a 2M aqueous solution of NaOH. After stirring for 2 h, the pH was adjusted to 6.5 using aqueous HCl and the solvents were evaporated. The product was purified using preparative HPLC. Yield: 68 mg (44%).

MS (ESP, m/e): 1349 (M$^+$, 15%), 1372 ([M+Na]$^+$, 100%).

EXAMPLE 20

N-Hydroxyacetyl-3-(1,2-dihydroxyethyl)-5-(2,3-dihydroxypropylaminocarbonyl)-2,4,6-triiodoaniline a. 3-Nitro-5-(2-trimethylsilylvinyl)benzoic acid methyl ester A mixture of 3-iodo-5-nitrobenzoic acid methyl ester (307 mg, 1.0 mmol), Pd(OAc)$_2$ (67 mg, 0.30 mmol), triphenylphosphine (0.032 g, 0.60 mmol), AgNO$_3$ (170 mg, 1.0 mmol), triethylamine (0.167 ml, 1.2 mmol) and vinyltrimethylsilane (0.309 ml, 2.0 mmol) was dissolved in acetonitrile (10 ml) and the solution was heated to 60° C. in a closed vessel for 48 h. The precipitated salts were filtered off and the filtrate was evaporated. The residue was chromatographed on silica gel using a mixture of ethyl acetate and heptane (1:11) as the eluent. Yield: 210 mg (75%).

$^1$H NMR (CDCl$_3$): 8.70–8.73 (m, 1H), 8.36–8.47 (m, 2H), 6.93 (d, J=19.2 Hz, 1H), 6.75 (d, J=19.2 Hz, 1H), 3.99 (s, 3H), 0.20 (s, 9H).

MS (APci, m/e): 279 (M$^+$, 100%).

b. 3-Nitro-5-vinylbenzoic acid methyl ester

3-Nitro-5-(2-trimethylsilylvinyl)benzoic acid methyl ester (2.44 g, 8.71 mmol) was dissolved in acetonitrile (150 ml), the solution was heated to reflux temperature and HCl gas was bubbled through the solution until the starting material had disappeared according to HPLC analysis. The solution was allowed to cool and the solvent was removed by evaporation. The residue was >95% pure according to HPLC and was used without further purification. Yield: 2.02 g (89%).

$^1$H NMR (CD$_3$CN): 8.64 (s, 1H), 8.54 (s, 1H), 8.45 (s, 1H), 6.96 (dd, J$_1$=10.8 Hz, J$_2$=17.4 Hz, 1H), 6.11 (d, J=17.4 Hz, 1H), 5.59 (d, J=10.8 Hz, 1H), 4.00 (s, 3H).

c. 3-Nitro-5-(1,2-dihydroxyethyl)benzoic acid methyl ester

3-Nitro-5-vinylbenzoic acid methyl ester (2.02 g, 9.76 mmol) was dissolved in a mixture of acetone and water (200 ml, 9:1), and, after cooling to 0° C., OsO$_4$ (60 mg, 0.24 mmol) was added followed by N-methylmorpholine-N-oxide (2.34 g, 20.0 mmol). After stirring for 46 h at room temperature, an aqueous solution of Na$_2$S$_2$O$_5$ (3.7 g) in water (150 ml) was added and the solution was acidified with dilute aqueous HCl. The volume of the solution was reduced to 150 ml by evaporation and the residue was extracted with ethyl acetate (3×100 ml). The combined organic phases were evaporated and the residue was purified by column chromatography on silica gel using ethyl acetate as the eluent. Yield: 1.60 g (60%).

$^1$H NMR (CD$_3$CN): 8.62–8.66 (m, 1H), 8.44–8.48 (m, 1H), 8.36–8.40 (m, 1H), 4.88–4.94 (m, 1H), 3.98 (s, 3H), 3.60–3.79 (m, 4H).

d. 1-(2,3-Dihydroxypropylaminocarbonyl)-3-nitro-5-(1,2-dihydroxyethyl)benzene

3-Nitro-5-(1,2-dihydroxyethyl)benzoic acid methyl ester (0.40 g, 1.69 mmol) and 2,3-dihydroxypropylamine (0.17 g, 1.86 mmol) were dissolved in methanol (2 ml) and the solution was stirred at 75° C. for 1 h. The pressure was then reduced to 200 mm Hg and stirring was continued at 95° C. for 2 h. The crude reaction mixture was purified by preparative HPLC. Yield: 0.40 g (78%).

MS (ESP. m/e): 299 ([M−1]$^+$, 100%).

e. 3-(2,3-Dihydroxypropylaminocarbonyl)-5-(1,2-dihydroxyethyl)aniline 1-(2,3-Dihydroxypropylaminocarbonyl)-3-nitro-5-(1,2-dihydroxyethyl)benzene (0.40 g, 1.32 mmol) was dissolved in a mixture of methanol (40 ml) and water (20 ml). The solution was hydrogenated at 60 psi using a Pd/C catalyst (10%, 50 mg). The solution was filtered through celite and the solvents were removed by evaporation. The product was >95% pure by HPLC analysis and was used without further purification.

MS (ESP, m/e): 271 ([M+1]$^+$, 100%), 293 ([M+Na]$^+$, 45%).

f. 3-(2,3-Dihydroxypropylaminocarbonyl)-5-(1,2-dihydroxyethyl)-2,4,6-triiodoaniline 3-(2,3-Dihydroxypropylaminocarbonyl)-5-(1,2-dihydroxyethyl)aniline (0.37 g, 1.35 mmol) was dissolved in a mixture of methanol (30 ml) and water (90 ml). KICl$_2$ (1.37 g, 4.05 mmol) was added and the solution was stirred at 35° C. for 24 h. Additional KICl$_2$ (1.0 mmol) was added, and stirring was continued at 60° C. for 72 h. An aqueous solution of Na$_2$S$_2$O$_5$ (1.0 g in 50 ml) was added and the solvents were removed by evaporation. Purification by preparative HPLC gave 87 mg (10%) of the pure product.

$^1$H NMR (CD$_3$OD): 8.60 (m, 1H), 5.38–5.47 (m, 1H), 3.96–4.26 (m, 3H), 3.30–3.84 (m, 10H).

MS (ESP, m/e): 648 (M$^+$, 15%), 670 ([M+Na]$^+$, 100%).

g. N-Hydroxyacetyl-3-(2,3-dihydroxypropyl aminocarbonyl)-5-(1,2-dihydroxyethyl)-2,4,6-triodoaniline 3-(2,3-Dihydroxypropylaminocarbonyl)-5-(1,2-dihydroxyethyl)-2,4,6-triodoaniline (0.059 d, 0.091 mmol) was mixed with acetoxyacetyl chloride (1.0 ml) containing N,N-dimethylacetamide (0.4 ml) and the mixture was stirred at 60° C. for 48 h. The mixture was allowed to cool to room temperature, water was added and the solvents were removed by evaporation. The residue was dissolved in a mixture of methanol (10 ml) and water (5 ml) and an aqueous solution of NaOH (5M, 1 ml) was added. The solution was stirred at room temperature for 1 h, the solution was neutralized with aqueous HCl and the solvents were evaporated. Purification by HPLC gave the pure product.

MS (ESP, m/e): 706 (M$^+$, 100%).

EXAMPLE 21

3,5-Di(hydroxyacetylamino)-2,4,6-triiodoacetophenone a. 1,3-Diamino-5-(1-hydroxyethyl)benzene 3,5-Dinitroacetophenone (2.02 g, 9.5 mmol) which had been prepared according to the literature procedure (Y. Nagase et al., Macromol. Chem. Rapid Comm. (1990) 11, 185–191) was dissolved in methanol (100 ml) and hydrogenated at 60 psi using a Pd/C catalyst (5%, 100 mg). The catalyst was filtered off and the solvent was removed by evaporation. The product was used without purification in the next step. Yield: 1.22 g (84%).

$^1$H NMR (CDCl$_3$): 6.20 (d, J=2.0 Hz, 2H), 6.08 (t, J=2.0 Hz, 1H), 4.90 (br s, 4H), 4.62 (q, J=7.0 Hz, 1H), 3.37 (d, J=7.0 Hz, 3H).

MS (ESP, m/e): 151 ([M−1]$^+$, 100%).

b. 1,3-Diamino-2,4,6-triiodoacetophenone 1,3-Diamino-5-(1-hydroxyethyl)benzene (1.18 g, 7.72 mmol) was dissolved in a mixture of methanol and water (5:1, 168 ml) containing 1M aqueous HCl (16 ml). An aqueous solution of KICl$_2$ (7.31 g, 30.9 mmol) was added quickly, and, after stirring for 50 min, the solid was filtered off, washed with water and dried. The product was pure by TLC and $^1$H NMR analysis. Yield: 3.62 g (89%).

$^1$H NMR CDCl$_3$): 4.86 (br s, 4H), 2.62 (s, 3H).

$^{13}$C NMR (CDCl$_3$): 204.7, 151.1, 146.8, 28.7.

MS (APci, m/e): 528 (M$^+$, 100%).

c. 1,3-Di(acetoxyacetylamino)-2,4,6-triiodoacetophenone 1,3-Diamino-2,4,6-triiodoacetophenone (1.8 g, 3.41 mmol) was dissolved in dimethylacetamide (15 ml) containing acetoxyacetyl chloride (1.1 ml, 10.2 mmol) and the solution was stirred for 65 h at room temperature. The solvents were removed by evaporation and the residue was purified by preparative HPLC. Yield: 1.69 g (68%).

$^1$H NMR DMSO-d$_6$): 10.13–10.27 (m, 2H), 4.65 (s, 4H), 2.56 (s, 3H), 2.12 (s, 6H).

MS (ESP, m/e): 750 ([M+Na]$^+$, 100%), 766 ([M+K]$^+$, 26%).

d. 1,3-Di(hydroxyacetylamino)-2,4,6-triiodoacetophenone 1,3-Di(acetoxyacetylamino)-2,4,6-triiodoacetophenone (0.171 g, 0.23 mmol) was dissolved in a mixture of methanol (30 ml) and water (5 ml) containing 2M aqueous NaOH (3 ml). The solution was stirred for 90 min and was then neutralized using a strongly acidic cation exchange resin. The solvents were removed by evaporation and the residue was purified by preparative HPLC. Yield: 98 mg (54%).

MS (ESP, m/e): 644 (M$^+$, 100%), 666 ([M+Na]$^+$, 95%).

EXAMPLE 22

3,5-Di(hydroxyacetylamino)-1-hydroxyacetyl-2,4,6-triiodobenzene a. 3,5-Di(acetoxyacetylamino)-1-bromoacetyl-2,4,6-triiodobenzene 1,3-Di(acetoxyacetylamino)-2,4,6-triiodoacetophenone (0.20 g, 0.279 mmol) was dissolved in glacial acetic acid and bromine (0.044 g, 0.28 mmol) was added. The reaction was stirred at 2.5 h at 75° C. and then allowed to cool. The solvents were removed by evaporation and the residue was used directly in the next step.

MS (ESP, m/e): 806 (M$^+$, 100%), 808 (M$^+$, 98%).

b. 3,5-Di(acetoxyacetylamino)-1-acetoxyacetyl-2,4,6-triiodobenzene 3,5-Di(acetoxyacetylamino)-1-bromoacetyl-2,4,6-triiodobenzene (10 mg, 0.12 mmol) was converted into the corresponding acetate by heating to 110° C. in glacial acetic acid (5 ml) containing sodium acetate (1 mmol) and AgOCOCF$_3$ (0.11 g, 0.5 mmol) for 16 h. The product was purified by preparative HPLC. The yield was not determined.

MS (ESP, m/e): 786 (M$^+$, 100%).

c. 3,5-Di(hydroxyacetylamino)-1-hydroxyacetyl-2,4,6-triiodobenzene

Hydrolysis of 3,5-di(acetoxyacetylamino)-1-acetoxyacetyl-2,4,6-triiodobenzene was carried out analogous to Example 4e. The crude product was purified by preparative HPLC. The yield was not determined.

MS (ESP, m/e): 687 ([M+HCOOH]$^+$, 100%).

EXAMPLE 23

3,5-Di(hydroxyacetylamino)-1-(1,2-dihydroxyethyl)-2,4,6-triiodobenzene a. 3,5-Dinitrophenylethanol 3,5-Dinitroacetophenone (3.27 g, 0.0156 mol) was dissolved in a mixture of absolute ethanol (75 ml) and THF (37.5 ml) and the mixture was cooled to −10° C. NaBH$_4$ (0.30 g, 7.9 mmol) was added and the mixture was stirred for 1 h at −10° C. Water (80 ml) and ethyl acetate were added, the phases were separated and the organic phase was washed with water (80 ml) and dried (Na$_2$SO$_4$). The solvents were removed by evaporation and the residue was purified by chromatography on neutral alumina using a is mixture of pentane and ethyl acetate (1:1) as the eluent. Yield: 2.52 g (76%).

$^1$H NMR (CDCl$_3$): 8.95 (t, J=2.0 Hz, 1H), 8.60 (d, J=2.0 Hz, 1H), 8.59 (d, J=2.0 Hz, 1H), 5.15 (q, J=7.5 Hz, 1H), 1.61 (d, J=7.5 Hz, 3H).

b. 3,5-Dinitrostyrene 3,5-Dinitrophenylethanol (1.0 g, 4.7 mmol) was mixed with P$_2$O$_5$ (1.0 g, 0.71 mmol) and the stirred mixture was heated to 100° C. After 3 h, the mixture was allowed to cool to room temperature and water (0.4 ml) was added. The pH was adjusted to 9 using 1M aqueous NaOH and extracted with diethyl ether (2×25 ml). The combined organic phases were dried (Na$_2$SO$_4$) and evaporated. The crude product was used without further purification in the next step.

$^1$H NMR CDCl$_3$): 8.92 (t, J=2.0 Hz, 1H), 8.56 (d, J=2.0 Hz, 2H), 6.86 (dd, J$_1$=18.4 Hz, J$_2$=10.9 Hz, 1H), 6.08 (d, J=18.0 Hz, 1H), 5.67 (d, J=10.9 Hz, 1H).

c. 1-(1,2-Dihydroxyethyl)-3,5-dinitrobenzene 3,5-Dinitrostyrene (0.50 g, 2.58 mmol) was dissolved in a mixture of acetone and water (8:1, 70 ml) and the solution was cooled to 0° C. OsO$_4$ (0.046 g, 0.18 mmol) and NMO (0.60 g, 5.15 mmol) were added and the solution was stirred at room temperature for 16 h. A solution of Na$_2$S$_2$O$_5$ (1.5 g) in water (120 ml) was added and the organic solvent removed by evaporation. The aqueous phase was extracted with ethyl acetate (2×70 ml) and the combined organic phases were dried (Na$_2$SO$_4$) and evaporated. The product was purified by preparative HPLC. Yield: 0.44 g (75%).

$^1$H NMR (CD$_3$CN): 8.87 (t, J=2.0 Hz, 1H), 8.63 (t, J=2.0 Hz, 2H), 4.98 (t, J=6.0 Hz, 1H), 3.64–3.79 (m, 2H), 2.34 (s, 2H).

MS (ESP$^−$, m/e): 227 (M$^−$, 50%), 197 ([M−CH$_2$O]$^−$, 100%).

d. 1-(1,2-Dihydroxyethyl)-3,5-diaminobenzene 1-(1,2-Dihydroxyethyl)-3,5-dinitrobenzene (0.10 g, 0.44 mmol) was dissolved in methanol (35 ml) and hydrogenation was carried out at 60 psi using a Pd/C catalyst (10%, 50 mg). The catalyst was filtered off and the solution was evaporated. Yield: 0.074 g (100%).

$^1$H NMR (CD$_3$OD): 6.14 (d, J=2.0 Hz, 2H), 6.06 (t, J=2.0 Hz, 1H), 4.98 (br s, 6H), 4.43–4.50 (m, 1H), 3.52–3.57 (m, 2H).

MS (ESP, m/e): 170 (M$^+$, 100%), 210 ([M+K]$^+$, 18%).

e. 1-(1,2-Dihydroxyethyl)-3,5-diamino-2,4,6-triiodobenzene 1-(1,2-Dihydroxyethyl)-3,5-diaminobenzene (0.0584 g, 0.242 mmol) was dissolved in a mixture of methanol (5 ml)

and aqueous 2M HCl (1.2 ml) and a solution of KICl$_2$ (70% in water, 0.97 mmol) was added in one portion.

After stirring for 20 min at room temperature, a 10% aqueous NaHSO$_3$ solution (0.2 ml) was added, the solvents were removed by evaporation and the residue was purified by preparative HPLC. Yield: 31.4 mg (24%).

$^1$H NMR (CD$_3$OD): 5.56–5.63 (m, 1H), 4.03–4.12 (m, 1H), 3.79–3.87 (m, 1H), 5.06 (br s, 4H).

f. 1-(1,2-Dihydroxyethyl)-3,5-di(hydroxyacetylamino)-2,4,6-triiodobenzene 1-(1,2-Dihydroxyethyl)-3,5-diamino-2,4,6-triiodobenzene is acylated with acetoxyacetyl chloride using for example such a procedure as described in Example 4d. The crude product is then hydrolyzed analogous to Example 4e to give the final product. Purification of the crude product is carried out using preparative HPLC.

We claim:

1. Compounds of formula (I)

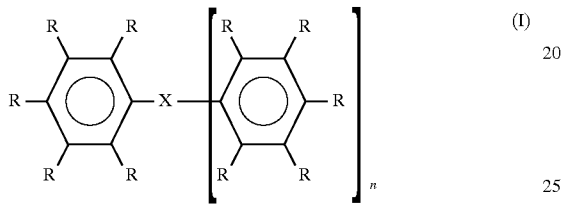

wherein:
- n is 0 or 1, and where n is 1 each C$_6$R$_5$ moiety may be the same or different;
- each group R is a hydrogen atom, an iodine atom or a hydrophilic moiety M or M$_1$, two or three non-adjacent R groups in each C$_6$R$_5$ moiety being iodine and at least one R group in each C$_6$R$_5$ moiety being M or M$_1$ moieties;
- X is a bond, an oxygen atom or a group NR$_1$, CO, CR$^1_2$, COCO, CONR$^1$, COCR$^1_2$, CR$^1_2$CR$^1_2$, CR$^1_2$NR$^1$, CR$^1_2$O, CONR$^1$CO, CONR$^1$CR$^1_2$, CR$^1_2$OCR$^1_2$, CR$^1_2$CONR$^1$, CR$^1_2$CR$^1_2$CR$^1_2$, COCR$^1$R$^1$CO, CR$^1_2$NR$^1$CR$^1_2$, or OCR$^1_2$CO, where R$^1$ is hydrogen or a C$_{1-6}$-alkyl or alkoxy group optionally substituted by hydroxy, alkoxy, oxa or oxo, and, where it is attached to a carbon atom, R$^1$ may also be a hydroxyl group;
- or, where n is 0, X denotes a group R;
- each M independently is a non-ionic hydrophilic moiety which is selected from the group consisting of
  —CONH—CH$_2$CH$_2$OH,
  —CONH—CH$_2$CHOHCH$_2$OH,
  —CONH—CH(CH$_2$OH)$_2$,
  —CON(CH$_2$CH$_2$OH)$_2$,
  —CONH$_2$,
  —CONHCH$_3$,
  —OCOCH$_3$,
  —N(COCH$_3$)H,
  —N(COCH$_3$)C$_{1-3}$-alkyl,
  —N(COCH$_3$)-mono, bis or tris-hydroxy C$_{1-4}$-alkyl,
  —N(COCH$_2$OH)-mono, bis or tris-hydroxy C$_{1-4}$-alkyl,
  —N(COCH$_2$OH)$_2$,
  —CON(CH$_2$CHOHCH$_2$OH) (CH$_2$CH$_2$OH),
  —CONH—C(CH$_2$OH)$_3$, and
  —CONH—CH(CH$_2$OH) (CHOHCH$_2$OH);

and
- each M$_1$ independently represents a C$_{1-4}$-alkyl group substituted by at least one hydroxyl group and optionally linked to the phenyl ring via a carbonyl, sulphone or sulphoxide group;
- with the proviso that where n is 0 either at least one M$_1$ group other than a hydroxymethyl or 1,2-dihydroxyethyl group is present or, if one hydroxymethyl or 1,2-dihydroxyethyl M$_1$ group is present, at least one nitrogen-attached hydroxylated C$_{1-4}$-alkyl moiety-containing M group is also present;
- or isomers thereof; at least one R group being an M$_1$ moiety.

2. Compounds as claimed in claim 1 wherein n is 1.

3. Compounds as claimed in claim 2 wherein at least one R group in each C$_6$R$_5$ moiety is an M$_1$ moiety.

4. Compounds as claimed in claim 2 wherein X is an asymmetric group.

5. Compounds as claimed in claim 2 wherein the two C$_6$R$_5$ groups are different.

6. Compounds as claimed in claim 1 wherein n is zero and the phenyl ring is asymmetrically substituted.

7. Compounds as claimed in claim 2 wherein one C$_6$R$_5$ group is of formula

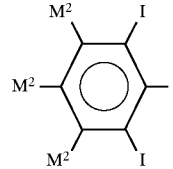

where each M$^2$ independently is a group M or M$^1$.

8. Compounds as claimed in claim 2 wherein one C$_6$R$_5$ group is of formula

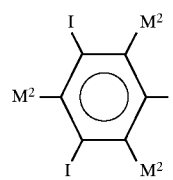

where each M$^2$ independently is a group M or M$^1$.

9. Compounds as claimed in claim 2 wherein each C$_6$R$_5$ group is of formula

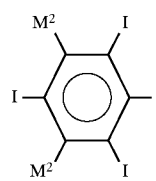

where each M$^2$ independently is a group M or M$^1$.

10. Compounds as claimed in claim 1 wherein the M$_1$ groups are selected from C$_{1-4}$-alkyl groups substituted by 1, 2, 3 or 4 hydroxy groups and optionally connected to the phenyl ring via a CO, SO or SO$_2$ group.

11. Compounds as claimed in claim 1 wherein the M$_1$ groups are selected from hydroxymethyl, 2-hydroxyethyl, 2,3-bishydroxy-propyl, 1,3-bishydroxyprop-2-yl, 2,3,4-trihydroxybutyl, 1,2,4-trihydroxybut-2-yl, COCH$_2$OH and SO$_2$CH$_2$OH.

12. A diagnostic composition comprising a compound of formula I as defined in claim 1 together with at least one physiologically tolerable carrier or excipient.

13. A compound as claimed in claim 1 which is N,N'-Bis(hydroxyacetyl)-N,N'-bis(2-hydroxyethyl)-3,5-diamino-2,4,6-triiodobenzyl alcohol.

* * * * *